(12) United States Patent
Choate

(10) Patent No.: US 10,143,371 B2
(45) Date of Patent: Dec. 4, 2018

(54) EYE EXAMINATION DEVICE

(71) Applicant: Myco Industries, Inc., Milford, MI (US)

(72) Inventor: John R. Choate, Milford, MI (US)

(73) Assignee: MYCO INDUSTRIES, INC., Milford, MI (US)

( * ) Notice: Subject to any disclaimer, the term of this patent is extended or adjusted under 35 U.S.C. 154(b) by 56 days.

(21) Appl. No.: 14/618,408

(22) Filed: Feb. 10, 2015

(65) Prior Publication Data
US 2016/0228001 A1 Aug. 11, 2016

(51) Int. Cl.
*A61B 3/14* (2006.01)
*A61B 3/00* (2006.01)
*A61B 3/15* (2006.01)

(52) U.S. Cl.
CPC .............. *A61B 3/14* (2013.01); *A61B 3/0008* (2013.01); *A61B 3/0025* (2013.01); *A61B 3/154* (2013.01)

(58) Field of Classification Search
CPC ....... A61B 3/14; A61B 3/0008; A61B 3/0025; A61B 3/154
USPC ........................................................ 351/206
See application file for complete search history.

(56) References Cited

U.S. PATENT DOCUMENTS

| | | | |
|---|---|---|---|
| D286,092 S | 10/1986 | Weimar | |
| 4,750,831 A | 6/1988 | Vega | |
| 4,953,970 A * | 9/1990 | Telchin | A61B 3/0008 351/223 |
| 5,442,488 A * | 8/1995 | Pastorino | A45D 42/08 359/802 |
| 6,010,488 A * | 1/2000 | Deas | A61B 17/0231 600/236 |
| 6,144,508 A | 11/2000 | Bransome | |
| 2007/0291225 A1* | 12/2007 | Suzuki | A61B 3/1208 351/206 |
| 2013/0128223 A1* | 5/2013 | Wood | A61B 1/0019 351/206 |
| 2015/0230703 A1* | 8/2015 | Wharton | A61B 3/13 351/221 |

* cited by examiner

*Primary Examiner* — William R Alexander
*Assistant Examiner* — Grant Gagnon
(74) *Attorney, Agent, or Firm* — Brooks Kushman P.C.

(57) ABSTRACT

An eye examination device may include a body defining a handle and a retainer for a mirror. The device may further include a projection having a predefined length from the body. The predefined length of the projection is defined by a focal length of the mirror. The device may further include a light integrated in the retainer adjacent to the mirror.

22 Claims, 4 Drawing Sheets

EYE EXAMINATION DEVICE

TECHNICAL FIELD

This disclosure relates to a portable apparatus for self-viewing of the eye.

BACKGROUND

Sufferers of diseases of an eye, for instance a person suffering from blepharitis, may need to inspect the eye closely for indications of its condition. Visual inspection of an eye disease may provide evidence of where the buildup of debris and/or bacteria is located and causing irritation to the eye. People who suffer from these diseases may need to visit an eye doctor to closely monitor the visual condition of the eye regularly. People who visit an eye doctor for treatment of this condition may be sent home to perform the current standard of care for management of blepharitis, which is to perform home lid scrubs on both eyes at least once a day. Home lid scrubs involve scrubbing one's own eyes and eyelashes with a non-irritating baby shampoo or other over the counter lids cleaning solution to remove the debris and bacteria from their eyelids and eyelashes. Individual home lid scrub procedures are often not adequate to remove all of the scurf, debris and bacteria from the eyelashes and eyelids without visual confirmation that each singular eyelash follicle is clean and free of any debris. While it may be possible of course to have one's eye condition checked daily by a doctor, for a variety of reasons it is not convenient or finically feasible to visit a doctor at a frequency that may be required.

People who may not suffer from such diseases but may simply wear contact lenses may have a need to inspect the eye. Contact lenses often encounter problems with debris or air bubbles between the lenses and the eye, which can lead to irritation of the surface of the eye, pain, and potential permanent damage to the cornea.

Self-inspection of the eye may be required for these and many other purposes which may be impossible to accomplish alone. There is a need for a device that may magnify to an extent required to observe sufficient detail of the eye, eyelid, eyelash, and surrounding area. An unresolved need therefore exists for an easy to use device for the self-visual inspection of the condition of the eye.

SUMMARY

In at least one embodiment, an eye examination device may include a body defining a handle. The device may have a mirror connected to the body. The device may further include a projection extending from the body adjacent to the mirror for cooperating with a user's face. The projection may have a predefined length from the body. The predefined length of the projection is defined by a focal length of the mirror. The device may further include a light integrated in the body adjacent to the mirror.

In at least one embodiment, a self-eye examination method for an eye examination device, the method provides a projection on the device to assist with examining the eye. The eye examination device includes a mirror coupled to a body and having at least one light adjacent to the mirror. The body defining a handle and having the projection configured to be placed on a cheek of a user. The method includes positioning the mirror over an eye using the handle with the projection on the user's check for positioning the user's eye proximate a focal point of the mirror. The method further includes inspecting an external region surrounding the user's eye.

In at least one embodiment, a reflective self-viewing device for an eye surface having a body including a handle and a mirror. The handle configured to have a control switch to operate a light. The body further includes a projection extending from the body and configured to be placed on a check of a user. The projection allowing a length defined by a focal length of the mirror. The body further including a light integrated in the projection and is operated by the control switch configured with the handle.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description given below serve to explain the disclosure.

DETAILED DESCRIPTION

Embodiments of the present disclosure are described herein. It is to be understood, however, that the disclosed embodiments are merely examples and other embodiments can take various and alternative forms. The figures are not necessarily to scale; some features could be exaggerated or minimized to show details of particular components. Therefore, specific structural and functional details disclosed herein are not to be interpreted as limiting, but merely as a representative basis for teaching one skilled in the art to variously employ the embodiments. As those of ordinary skill in the art will understand, various features illustrated and described with reference to any one of the figures can be combined with features illustrated in one or more other figures to produce embodiments that are not explicitly illustrated or described. The combinations of features illustrated provide representative embodiments for typical applications. Various combinations and modifications of the features consistent with the teachings of this disclosure, however, could be desired for particular applications or implementations.

The embodiments of the present disclosure generally provide for a plurality of circuits or other electrical devices. All references to the circuits and other electrical devices and the functionality provided by each, are not intended to be limited to encompassing only what is illustrated and described herein. While particular labels may be assigned to the various circuits or other electrical devices disclosed, such labels are not intended to limit the scope of operation for the circuits and the other electrical devices. Such circuits and other electrical devices may be combined with each other and/or separated in any manner based on the particular type of electrical implementation that is desired. It is recognized that any circuit or other electrical device disclosed herein may include any number of microprocessors, integrated circuits, memory devices (e.g., FLASH, random access memory (RAM), read only memory (ROM), electrically programmable read only memory (EPROM), electrically erasable programmable read only memory (EEPROM), or other suitable variants thereof) and software which co-act with one another to perform operation(s) disclosed herein. In addition, any one or more of the electric devices may be configured to execute a computer-program that is embodied in a non-transitory computer readable medium that is programmed to perform any number of the functions as disclosed.

This disclosure describes an eye examining device comprising a mirror, a light (e.g., light-emitting diode (LED), incandescent light bulb, etc.), and a projection (i.e., a separator bar). The LED may be integrated on the device to indirectly illuminate eye lids, lashes and cornea. The separator bar may be designed to keep the mirror far enough away so that the user may view the eye efficiently. The separator bar may be foldable onto a front side of the device when not being used. The separator bar may be configured for the user to rest the bar on the user's (or a patient's) cheek. The separator bar may have the LED integrated onto the bar to minimize direct illumination through the pupil into the eye.

The eye examining device comprises the separator bar designed to use an LED to examine the eye and/or surrounding area at the right distance. For example, a user suffering from an eye disease may visual inspect the eye to detect debris at the base and around the eyelashes with the use of the device. The separator bar provides assistance to the user for positioning the device at the right distance and location to inspect the eye and the surrounding area. The device provides a magnified view of the eye and surrounding area with the help of the separator bar operated to help position mirror over the eye.

In one embodiment, the eye examining device may be integrated with a digital camera to enable the user to take a picture and/or video of the eye. The eye examining device may also include a lithium ion battery with a charging base, Bluetooth wireless printing capabilities, and/or a USB output adapter with auto configure software to view the image when connected to computer.

Figure 1:
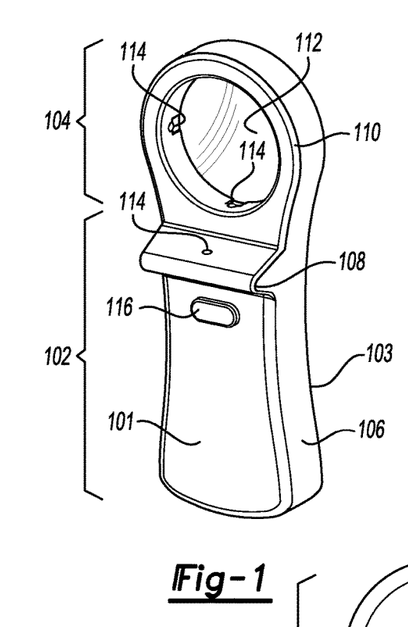
FIG. 1 is a perspective drawing of one embodiment of a device.

FIG. 1 is a perspective drawing of one embodiment of the device 100. An embodiment of the device 100 for examining an eye includes a body 102 and a retainer 104. The body 102 portion may house at least one of a power supply, a control circuit, and/or a combination thereof. The body 102 is configured to include a handle 106 which enables a user to position the device 100 so that a focal point of a mirror 112 is proximately placed over the eye. The body 102 may have a projection 108 (i.e., separator bar) extending therefrom to assist the user in positioning the mirror over the eye at the right distance. The mirror 112 is housed in the retainer 104 of the device 100. The mirror 112 may range from a two-time to a forty-time magnification mirror. In one embodiment the mirror 112 may be a ten-time magnification mirror to provide inspection of the eye and the surrounding area.

As shown in FIG. 1, a light 114 (e.g., LED) may be positioned in the separator bar 108. In another embodiment, the retainer 104 may include one or more LEDs 114 positioned around the mirror 112. The one or more LEDs 114 may be configured to provide the appropriate lighting to examine the eye and surrounding area. The one or more LEDs positioned around the mirror will be discussed further in FIG. 2.

In at least one embodiment, the retainer 104 may provide a structure 110 to be formed to match the contour of an eye. For example, the structure 110 may be a circle that reaches from the inner corner of an eye to the outer corner below the end of an eyebrow, including the area underneath the eye as well as up to a brow bone. The structure 110 may have a mirror 112 and one or more LEDs 114 positioned therein.

As shown in FIG. 1, the device 100 may have a front side 101 and a back side 103. In one embodiment, the front side 101 may be manufactured as one piece having a front portion of the handle 102 and retainer 104. The front side 101 is configured to couple to the back side 103. The front side 101 of the device 100 may include the separator bar 108 configured to provide a predefined distance from the eye to the mirror 112 when the device is in use by a user. For example, the separator bar 108 is designed to be positioned underneath the user's eye to provide the optimal distance from the mirror 112 to the eye and to assist the user in pulling down their eyelids for better visualization of the eye. In one embodiment, the separator bar 108 may provide several predefined distances from the eye to the mirror 112. In another embodiment, the separator bar 108 may be foldable on the front side 101 of the device when not in use. The foldable separator bar 108 will be discussed further in FIG. 8.

The back side 103 of the device 100 may be manufactured as one piece having a back portion of the handle 102 and retainer 104. The back side 103 is configured to couple to the front side 101. The back side 103 of the device 100 may include a removable cover (not shown) that may provide access to a power source, such as batteries. The cover will be discussed further in FIG. 3. In an exemplary embodiment, the electric power source is a battery power source contained within the body. The battery power source may be either a removable disposable battery or a rechargeable battery. The electric power source operably provides electric power to the light 114 (e.g., LED(s)), which the operator controls via the control switch 116.

Furthermore, it will be appreciated that the device 100 may be manufactured from various materials suited to specific environments of use. For instance, operators such as mechanics, technicians, and/or construction personnel that operate in a harsh environment setting may desire the device 100 to be made from stainless steel and have a rechargeable battery. However, operators within the home treatment setting may desire a device 100 that is light weight (e.g., made from plastic) and have a removable disposable battery.

Figure 2:
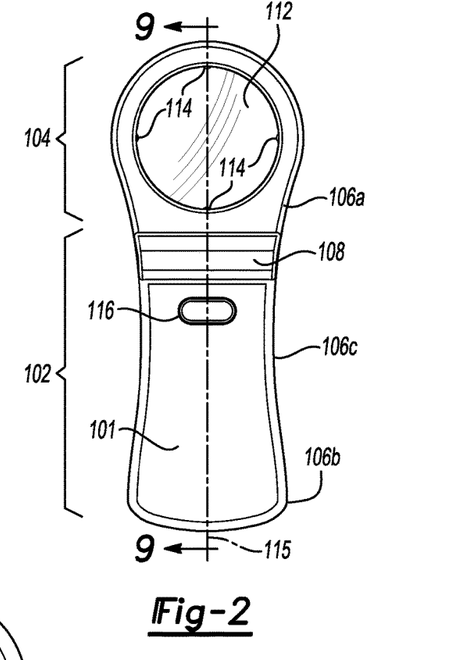
FIG. 2 is a front side view of the device of FIG. 1.

FIG. 2 is the front side 101 view of the device 100 of FIG. 1. The device 100 may include the body 102 configured as a contoured handle 106. The countered handle 106 may have a neck portion 106c which increases diameter towards the upper portion 106a and the lower portion 106b of the body 102 along an axis 115. The increase in diameter towards the upper portion 106a and the lower portion 106b of the body may be symmetric along the axis 115. For example, the neck portion 106 provides a contoured shape for handling the device 100 and to assist the user with the self-examination of the eye.

The device 100 may include the retainer 104 portion configured as a half circle structure 110. For example, the half circle structure 110 may be coupled to the body 102 such that a circular mirror 112 is secured and centered along the axis 115. The retainer 104 may have a structure 110 coupled to the body 102 and configured to support other mirror arrangements not limited to a circular structure 110 design. In another example, the retainer 104 may be a frame circumscribing one or more mirror configurations.

Figure 3:
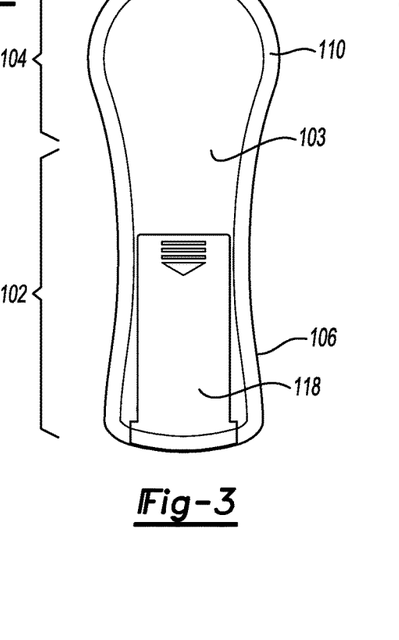
FIG. 3 is a back side view of the device of FIG. 1.

FIG. 3 is the back side 103 view of the device 100 of FIG. 1. The back side 103 provides the removable cover 118 for access to the power source. For example, the user may access disposable batteries by removing the cover 118 on the back side 103 of the device 100.

Figure 4:
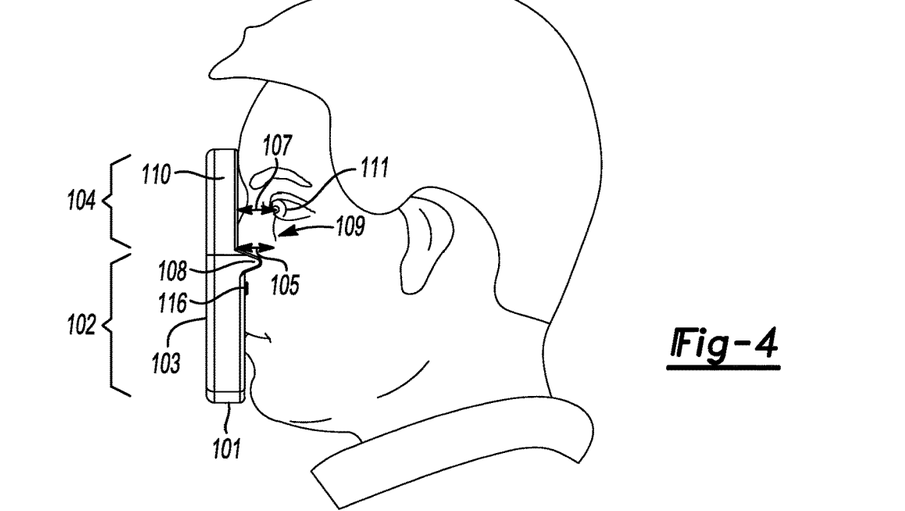
FIG. 4 is a side view of the device of FIG. 1.

FIG. 4 is a side view of the device of FIG. 1. The front side 101 of the device 100 includes the separator bar 108 adjacent to the structure 110 of the retainer 104 housing the mirror 112. As shown in FIG. 4, the separator bar 108 projects from the front side 101 of the device 100. The separator bar 108 may be configured to have a predetermined length 105 so that the user may accurately position the device 100 on the user's cheek 109 for self-examination. For example, the separator bar 108 may be designed such that the mirror may be at a predefined distance 107 from the eye 111 when the bar 108 is resting on the cheek 109 of the user. The predefined distance 107 may range from two millimeters to twenty-five millimeters.

In one embodiment, the separator bar 108 may have a length 105 of approximately eleven and a half millimeters being projected from the front side 101 of the device 100. With a length 105 of approximately eleven and a half millimeters, the separator bar 108 is resting on the check 109 such that the predefined distance 107 to the eye 11 may equal approximately fifteen millimeters. The user of the device may pull down the eyelids for better visualization of the eye with the use of the separator bar 108 resting on the cheek 109.

Figure 5:
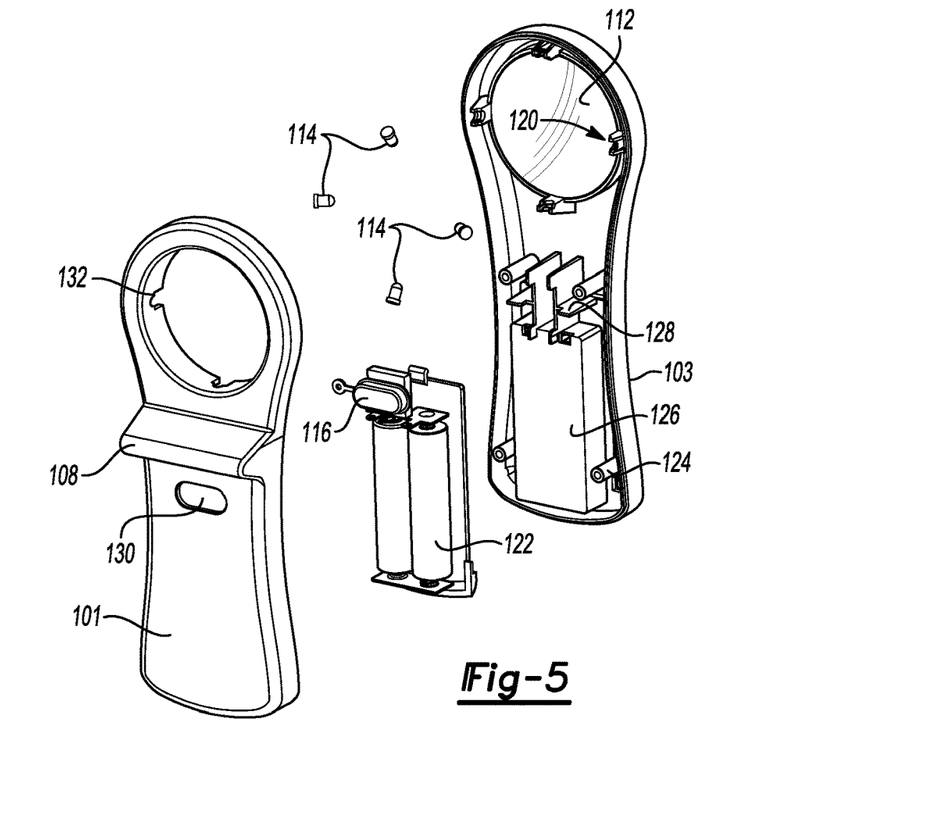
FIG. 5 is a partially exploded perspective view of the device.

FIG. 5 is a partially exploded perspective view of the device 100. The back side 103 of the device comprises one or more mounts 120 to secure the mirror 112. In one embodiment, the one or more mounts 120 may be configured to receive one or more LED(s) 114. For example, the LED(s) 114 may be positioned on the mount 120 and secured to the device 100 when the front side 101 is coupled to the back side 103. The front side 101 may have one or more slots 132 to expose the one or more LEDs 114 adjacent to the mirror 112. In another example, the device 100 may include an LED configured with a light pipe adjacent to the mirror. The device 100 comprising a light pipe configuration will be discussed further in FIG. 9.

As shown in FIG. 5, the back side 103 may contain one or more shafts 124 configured to provide coupling between the front side 101 and back side 103. For example, the device 100 may be configured to enable the front side 101 to be snapped together with the back side 103. In one embodiment, the snapping assembly of the front side 101 to the back side 103 of the device may not require glue. In another example, the shafts 124 may allow for one or more screws to be inserted for securing the front side 101 to the back side 103 of the device 100.

The back side 103 includes a base 126 to secure the power source 122 to the device 100. In addition to the power source base 126, the back side 103 is configured to provide a switch mount 128 for the control switch 116. The control switch 116 may be positioned through a slot 130 on the front side 101 of the device 100. The slot 130 provides the switch to be exposed on the front side 101 of the device 100 for access and control by a user.

In one embodiment, the device 100 may include a circuit for proving power via the power supply 122 to the light 114 based on the position of the control switch 116. The circuit may be housed in the body 102 of the device 100. In another embodiment, the device 100 may include a computing system having a camera to capture an image of the eye. The computing system may be housed in the body 102 of the device 100. The computing system will be discussed further in FIG. 6.

Figure 6:
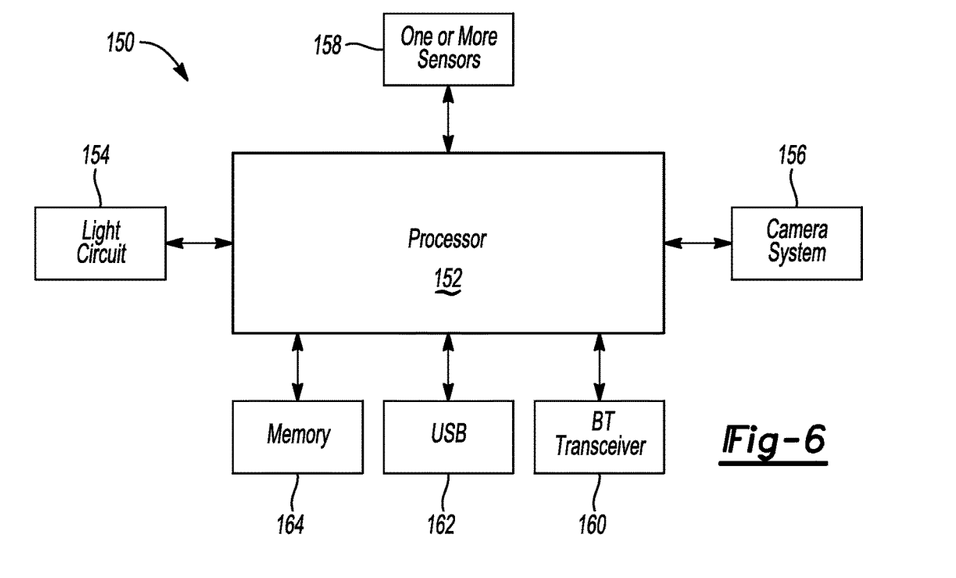
FIG. 6 is a drawing of a computing system for the device.

FIG. 6 is a drawing of a computing system 150 for the device 100. The computing system 150 may include, but is not limited to, a processor 152, an LED system 154, a camera system 156, one or more sensors 158, a wireless transceiver 160 (e.g., a Bluetooth transceiver), a universal serial bus (USB) 162, memory 164, and/or a combination thereof. The device 100 may comprise one or more algorithms executed on hardware of the computing system 150 to capture images of an eye using a camera via the camera system 156.

The processor may be configured to adjust the brightness of the one or more lights 114 (e.g., LED) via the light circuit 154. The processor may adjust the light 114 based on received brightness measurements for the surrounding area of the device 100 using one or more sensors 158 (e.g., a photodetector sensor). For example, in response to a brightness measurement via a photodetector sensor 158, the processor may increase the brightness of the light 114 to get a better image of the eye.

The processor 152 may control the camera system 156 to command still pictures and/or recorded video. The processor 152 may adjust the camera based on a measured distance from the mirror to the eye using a sensor 158 (e.g., a proximity sensor). For example, in response to a distance measurement from the device 100 to the eye via a proximity sensor, the processor 152 may request the camera to zoom in to capture the requested image. In another example, in response to the distance, the processor 152 may adjust the one or more lights 114 to allow for an optimal inspection and/or picture of the eye.

The processor 152 may be configured to communicate with memory 164 to store one or more images and/or videos of the eye. The memory 164 may include non-persistent storage such as random access memory (RAM) and the persistent storage is a hard disk drive (HDD) or flash memory. The memory 164 may store the one or more algorithms used to control the computer system 150.

The USB 162 is one of a class of serial networking protocols. IEEE 1394 (FireWire™ (Apple), i.LINK™ (Sony), and Lynx™ (Texas Instruments)), EIA (Electronics Industry Association) serial protocols, IEEE 1284 (Centronics Port), S/PDIF (Sony/Philips Digital Interconnect Format) and USB-IF (USB Implementers Forum) form the backbone of the device-device serial standards. Most of the protocols may be implemented for either electrical or optical communication. The system 150 may communicate the data received at the device 100 to one or more outputs via the USB 162. The system 150 may communicate the data received at the device 100 to one or more outputs via a wireless transceiver 160. For example, the device 100 may capture one or more images of the eye via the camera system 156 and may wirelessly transmit the images to a remote computer via the Bluetooth transceiver 160. The computer system integrated within the device 100 will be discussed further in FIG. 9.

Figure 7:
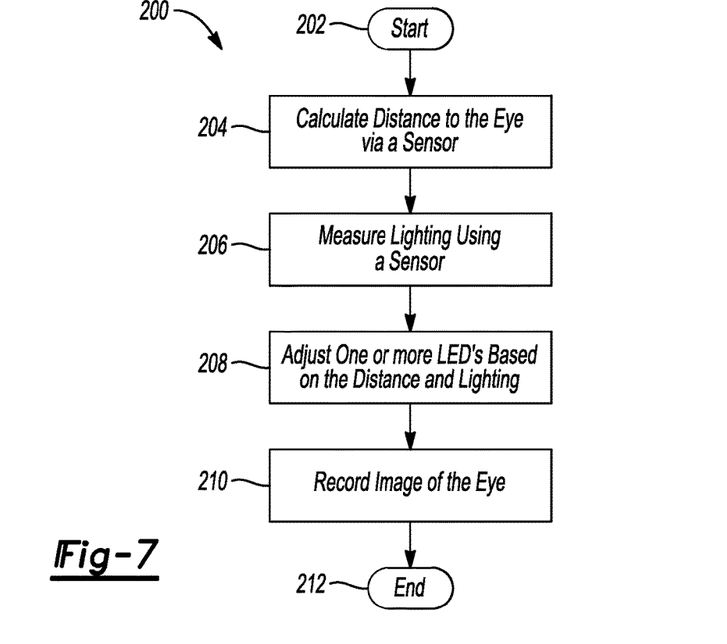
FIG. 7 is a flow chart illustrating an exemplary process for an eye examination using the device.

FIG. 7 an exemplary process for the eye examination device 100. The process 200 may be implemented using software code contained within one or more processors located on the device 100. In other embodiments, the process 200 may be implemented in other processors in communication with the device 100.

Referring again to FIG. 7, the device 100 and its components illustrated in FIG. 1-FIG. 6 are referenced throughout the description of the process to facilitate understanding of various aspects of the present disclosure. The process 200 of examination of an eye using the device 100 may be implemented through a computer algorithm, machine executable code, or software instructions programmed into a suitable programmable logic machine of the device 100, such as the processor, another processor in communication with the device, or a combination thereof. Although the various operations shown in the flowchart diagram 200 appear to occur in a chronological sequence, at least some of the operations may occur in a different order, and some operations may be performed concurrently or not at all.

In operation 202, system 150 may be initialized based on the control switch 116 being turned to the on position. The system 150 may calculate a distance to the eye via a sensor 158 (e.g., proximity sensor) in operation 204.

For example, the device 100 is placed in position over the eye by using the separator bar projection 108 on the cheek of the user. The separator bar projection 108 assists with placing the focal point of the mirror at a proximate position with the eye such that the user may inspect the eyelids, eyelashes, and the surrounding area. In response to the device 100 in position over the eye, the system may calculate a distance from the mirror to the eye via the proximity sensor 158.

In operation 206, the system may measure the light surrounding the device 100 using a sensor 158 (e.g., photodetector). In response to the measured light, distance and/or the combination thereof, the system 150 may adjust the brightness of the one or more lights 114 in operation 208. For example, the system measures the surrounding brightness to ensure the intensity for the light 114 is set to a level that provides a user acceptable illumination to examine the eye and surrounding area.

In operation 210, the system 150 may record an image of the eye based on user input. The user may use the control switch 116 to request a picture to be taken using a camera 156 integrated on the device 100. In another embodiment, the device may have a camera switch to control taking images of the eye via the camera. For example, the user may request video of the eye inspection to be recorded using the camera 156 at the device 100 based on input received at the control switch 116 and/or camera switch.

In another example, the system 150 may capture images of the eye using the camera, and store the images in memory 164. The system 150 may be configured to transmit the images to a remote computer via a wired (e.g., USB 162) and/or wireless (e.g., Bluetooth transceiver 160) connection.

In operation 212, the system 150 may be requested for shutdown based on the control switch being turned off. In another example, the system 150 may be automatically disabled if no input is received from a user after a predefined amount of time. During shutdown of the system 150, the one or more images and/or video captured may be stored in memory 164.

Figure 8:
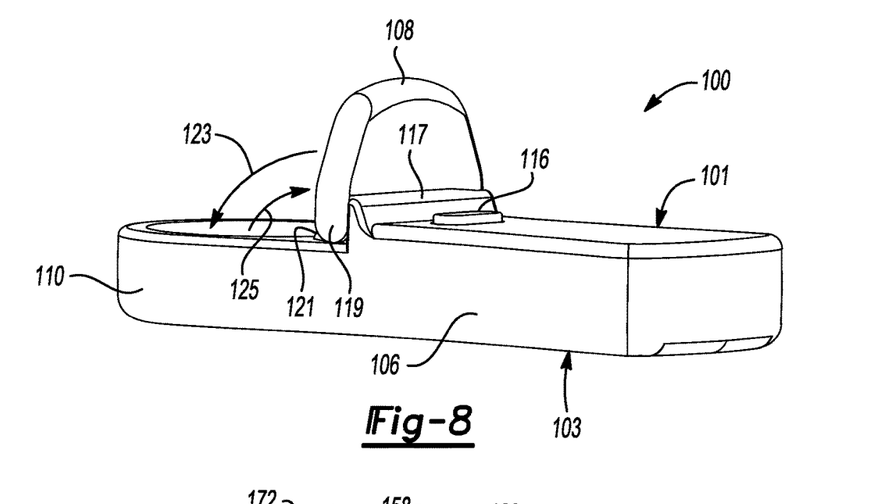
FIG. 8 is a perspective drawing of one embodiment of the device.

FIG. 8 is a perspective drawing of one embodiment of the device 100 having the foldable separator bar 108. The body 102 of the device 100 may have a pair of support arms 121 configured to attach to the separator bar 108. The separator bar 108 is pivotally connected 119 to the support arms 121. Based on the connection to the support arms 121, the separator bar 108 may follow the close and open arrows 123, 125 to provide an open and close position for the bar 108.

For example, following the close arrow 123, the separator bar 108 may be folded in a close position onto the front side 101 of the device 100 when not in use. The close position arranges the separator bar 108 to rest against the structure 110 of the mirror 112 approximately flush with the handle 106. The support arms 121 configured with the pivotal connection 119 may provide enough resistance to allow the separator bar 108 to stay in the closed position.

In another example, a user may apply force along the open arrow 125 may raise the separator bar 108 from the closed position to an open position via the pivotally connection 119 configured with the support arms 121. The open position arranges the separator bar 108 to rest against a bar stopper 117. The bar stopper 117 is configured to provide a fixed position for the separator bar 108. The support arms 121 configured with the pivotal connection 119 may provide enough resistance to allow the separator bar 108 to stay in the open position. For example, the support arms 121 may provide enough resistance to keep the bar 108 fixed in the open position such that the user may apply pressure against the handle pushing the separator bar 108 towards the cheek to pull down the eyelid.

Figure 9:
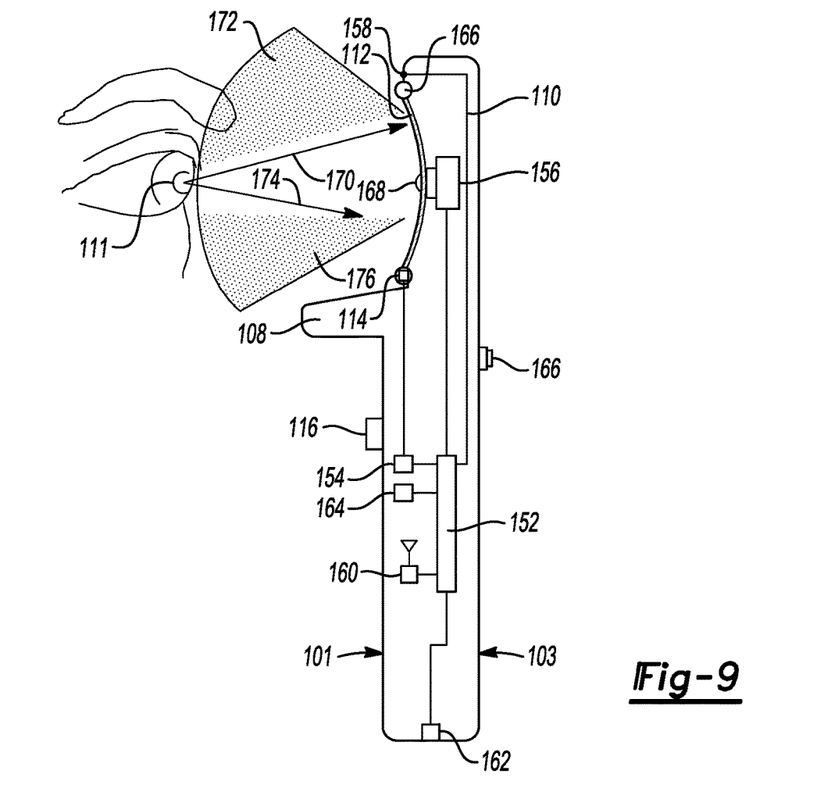
FIG. 9 is a sectional view of the device integrated with the computer system.

FIG. 9 is a sectional view 250 of the device 100 integrated with the computer system 150. As shown in FIG. 9, the section view 250 is taken along line 9-9 in FIG. 2. The device 100 may include one or more components of the computer system 150. The computer system 150 may include the processor 152, the light circuit 154, the camera system 156, the wireless transceiver 160, the USB port 162, memory 164, and a combination thereof.

The light system 154 may include the one or more lights 114 assembled with a light pipe 166. As shown in FIG. 9, a section of the light pipe 166 is illustrated as surrounding the mirror to provide light to the eye and surrounding area. The light pipe may be integrated within the structure 110 to border the mirror 112. The mirror 112 may have one or more curves to assist in the inspection of the eye and surrounding area. For example, the mirror 112 may be concave such that a user of the device 100 may view the upper and lower eyelashes and eyelids of the eye 111.

The camera system 156 may include a camera lens 168 positioned in the center of the mirror 112 so that the camera may capture a substantially direct image of the eye 111 and surrounding area. For example, the camera lens 168 may be positioned in the center of the mirror 112 not interfering with the ability to inspect the lower and upper regions of the eye and surrounding area. A user may control the camera system 156 using a camera switch 166 on the back side 103 of the device 100.

For example, the user may position the mirror 112 over the eye 111 using the separator bar 108. The user may turn on the light 114 of the light system 154 to illuminate the eye 111 and surrounding area via the control switch 116. In one embodiment, the processor may adjust the brightness of the light 114 based on one or more measurements at a sensor 158.

In another example, the user may request to take images or video recordings of the eye 111 and/or surrounding area of the eye 111 using the camera system 156. With the use of the separator bar 108, the user may position the device 100 at the eye 111 to take an accurate image of the eye 111. The user may control the functions of the camera system 156 via the camera switch 166. For example, the user may take pictures or record video of the eye 111 based on user input at the camera switch 166.

In response to one or more recorded images of the eye 111 via the camera system 156, the processor 152 may manage to store the image(s) in memory 164. In another example, the processor 152 may be configured to transmit the one or more images to a remote computer device via the wireless transceiver 160 and/or the USB port 162.

The device 100 may provide the user to inspect the eye 111 and surrounding areas using the concave mirror 112. For example, following an upper direction arrow 170, the eye 111 is looking at the top portion of the concave mirror 112. The eye 111 viewing the mirror 112 in the upper direction arrow 170 provides a reflection of an upper visual view 172 of the eyelid and eyelashes for inspection at the mirror 112. In another example, following a lower direction arrow 174, the eye 111 is looking at the bottom 174 of the concave mirror 112. The eye 111 viewing the mirror 112 in the lower direction arrow 174 provides a reflection of a lower visual view 176 of the eyelid and eyelashes for inspection at the mirror 112.

The camera system 156 may capture images not in the field of view of the eye 111. For example, if the eye is viewing the mirror 112 following the lower direction arrow 174, the user may not be capable of viewing the upper visual view 172 of the eye 111. The camera system 156 on the device 100 may capture the image so that the user may review the upper visual view 172 of the eye 111 when the eye's 111 line of sight follows the lower direction arrow 174. In another example, if the eye 111 is viewing the concave mirror 112 following the upper direction arrow 170, the user may not be capable of viewing the lower visual view 176 of the eye 111. The device 100 may capture the image so that the user may review the lower visual view 176 of the eye 111 when the eye's 111 line of sight follows the upper direction arrow 170. The captured images may be transmitted for viewing at a computing device via the wireless transceiver 160 and/or USB port 162.

The device 100 offers a method for a user to inspect the cleanliness of their eyelashes and eyelids. The device 100 may be used in many situations where inspection of the eye is required. For example, people who suffer from eye 111 diseases such as Blepharitis may use the device 100 to eliminate the debris at the base and around the eyelashes that may cause itchy, scratchy and irritated eyes. From mechanics working on machines to a user installing contact lens, the device 100 provides an ergonomically solution for a magnified close up view of the eye and surrounding area.

While exemplary embodiments are described above, it is not intended that these embodiments describe all possible forms encompassed by the claims. The words used in the specification are words of description rather than limitation, and it is understood that various changes can be made without departing from the spirit and scope of the disclosure. As previously described, the features of various embodiments can be combined to form further embodiments of the invention that may not be explicitly described or illustrated. While various embodiments could have been described as providing advantages or being preferred over other embodiments or prior art implementations with respect to one or more desired characteristics, those of ordinary skill in the art recognize that one or more features or characteristics can be compromised to achieve desired overall system attributes, which depend on the specific application and implementation. These attributes can include, but are not limited to cost, strength, durability, life cycle cost, marketability, appearance, packaging, size, serviceability, weight, manufacturability, ease of assembly, etc. As such, embodiments described as less desirable than other embodiments or prior art implementations with respect to one or more characteristics are not outside the scope of the disclosure and can be desirable for particular applications.

What is claimed is:

1. An eye self-examination device comprising:
   a body having frame portion and a handle extending downwardly therefrom;
   a concave mirror connected to the body frame portion; and
   a projection extending from the body in a limited region below the mirror to be placed on a user's cheek, the projection having a predefined transverse length extending below the eye to be examined, and a predefined height from the body defined by a focal length of the mirror, the projection enabling a user to pull down their eyelid to directly view a reflected image of his or her eye and eyelid area in the mirror without the projection obstructing ambient light from illuminating the user's eye and eyelid area.

2. The eye self-examination device of claim 1, further comprising a light attached to the body frame portion adjacent to a periphery of the mirror to illuminate the user's eye and eyelid area in low ambient light conditions, wherein the light is enabled using a control switch coupled to the handle.

3. The eye self-examination device of claim 1, wherein the mirror is a ten-time to a forty-time magnification mirror.

4. The eye self-examination device of claim 1, further comprising a power source housed in the body to power the light.

5. The eye self-examination device of claim 4, wherein the power source is at least one of a rechargeable battery and a removable battery.

6. The eye self-examination device of claim 1, wherein the predefined focal length is up to approximately seventy-five millimeters.

7. The eye self-examination device of claim 1, wherein the projection is configured to be foldable in a close position on the body.

8. The eye self-examination device of claim 1, further comprising a light coupled to a light pipe integrated with the body frame portion to illuminate the user's eye and eyelid area in low ambient light conditions.

9. The eye self-examination device of claim 8, wherein the body frame portion circumscribes the mirror.

10. The eye self-examination device of claim 1, further comprising a camera having a camera lens positioned in the center the mirror, and at least one processor configured to, in response to user input, control the camera to capture an image.

11. The eye examination device of claim 10, wherein the at least one processor is further configured to transmit the image to a computer via a universal serial bus.

12. The eye self-examination device of claim 10, further comprising a wireless transceiver, wherein the at least one processor is further configured to transmit the image via the wireless transceiver.

13. The eye self-examination device of claim 10, further comprising a camera and a photodetector, wherein the at least one processor is further configured to adjust the light based to a predefined threshold corresponding to the photodetector before the camera captures an image of the user's eye and eyelid area.

14. A self-eye examination method comprising:
   the user obtaining an eye examination device having a concave mirror coupled to a body, at least one light adjacent to the mirror, and the body having a projection limited to a location below the mirror configured to be placed on a cheek of a user;
   the user positioning the mirror over a user's eye using a handle extending downwardly from the body with the projection placed on the user's cheek to position an external region surrounding the user's eye proximate a focal point of the mirror;

the user pulling down their eyelid to directly view a reflected image of his or her eye and eyelid area in the mirror without obstructing ambient light from illuminating the user's eye and eyelid area; and the user inspecting an external region surrounding the user's eye by viewing using the eye being inspected in a reflected image of the eye in the mirror.

15. The method of claim 14, wherein the inspecting the image viewed in the mirror is magnified by the mirror having a predefined focal length of up to seventy-five millimeters.

16. The method of claim 14, further comprising capturing an image of the eye and the external region surrounding the user's eye with a camera a camera having a camera lens positioned in the center of the concave mirror.

17. The method of claim 14, further comprising illuminating the external region surrounding the user's eye.

18. A reflective self-viewing device for inspecting an external region surrounding the user's eye, the device comprising:

a body having frame portion and a handle extending downwardly therefrom configured to have a control switch;

a concave mirror connected to the body frame portion; and a projection extending from the body in a limited region below the mirror and configured to be placed on a cheek of a user, the projection provides a predetermined height defined by a focal length of the mirror to position the external region surrounding user's eye at a focal point of the mirror enabling the user to pull down their eyelid to directly view the self-examination by a user of a reflected image of the external region surrounding the eye without obstructing ambient light from illuminating the user's eye and eyelid area.

19. The device of claim 18, wherein the predetermined focal length of the mirror is not more than seventy-five millimeters.

20. The device of claim 18, further comprising a light integrated in the body or the projection and operated by the control switch configured with the handle to illuminate the external region surrounding the user's eye.

21. The device of claim 20, wherein the light is at least one of a light emitting diode and an incandescent light bulb.

22. The device of claim 20, wherein the light comprises a plurality of lights arranged about the concave mirror to illuminate the user's eye and the external region surrounding the eye.

* * * * *

UNITED STATES PATENT AND TRADEMARK OFFICE
CERTIFICATE OF CORRECTION

PATENT NO. : 10,143,371 B2
APPLICATION NO. : 14/618408
DATED : December 4, 2018
INVENTOR(S) : John R. Choate et al.

Page 1 of 1

It is certified that error appears in the above-identified patent and that said Letters Patent is hereby corrected as shown below:

In the Claims

Column 10, Line 3, Claim 1:
After "a body having"
Insert -- a --.

Column 11, Line 17, Claim 16:
After "user's eye with a camera"
Delete "a camera" (second occurrence).

Signed and Sealed this
Twenty-third Day of April, 2019

Andrei Iancu
*Director of the United States Patent and Trademark Office*